(12) United States Patent
Sahibzada (10) Patent No.: US 8,443,652 B2
(45) Date of Patent: May 21, 2013

(54) FLUID DETECTOR

(75) Inventor: Jörgen Sahibzada, Västra Frölanda (SE)

(73) Assignee: Calectro Aktiebolag, Vastra Frolunda (SE)

( * ) Notice: Subject to any disclaimer, the term of this patent is extended or adjusted under 35 U.S.C. 154(b) by 702 days.

(21) Appl. No.: 12/588,027

(22) Filed: Oct. 1, 2009

(65) Prior Publication Data

US 2011/0081852 A1    Apr. 7, 2011

(51) Int. Cl.
*G01N 7/00*    (2006.01)

(52) U.S. Cl.
USPC ...... 73/23.2; 73/863.51; 73/863.81; 439/112; 439/113; 439/114; 439/115; 439/119

(58) Field of Classification Search
USPC .............. 73/23.2, 863.21, 31, 41, 51, 57, 81, 73/864, 864.33, 5; 439/31, 165, 534, 713, 439/913; 340/603
See application file for complete search history.

(56) References Cited

U.S. PATENT DOCUMENTS

| | | | | |
|---|---|---|---|---|
| 4,758,827 A * | 7/1988 | Powers | ...................... | 340/691.7 |
| 5,773,726 A * | 6/1998 | Mahoney et al. | .......... | 73/861.65 |
| 5,873,357 A | 2/1999 | Lake | | |
| 6,145,392 A | 11/2000 | Kathan et al. | | |
| 6,508,131 B2 * | 1/2003 | Frick | ................ | 73/756 |
| 6,719,578 B1 * | 4/2004 | Klassen et al. | ................ | 439/289 |
| 7,322,827 B2 * | 1/2008 | Frawley et al. | ................. | 439/31 |
| 7,823,438 B2 * | 11/2010 | Sahibzada | ...................... | 73/23.2 |
| 2002/0011115 A1 | 1/2002 | Frick | | |
| 2009/0267357 A1 * | 10/2009 | Hall et al. | ...................... | 292/99 |

FOREIGN PATENT DOCUMENTS

| | | |
|---|---|---|
| DE | 102 21 931 | 11/2002 |
| DE | 298 25 224 | 7/2006 |
| DE | 10 2005 031 083 | 1/2007 |
| WO | WO 94/26352 | 11/1994 |
| WO | WO 99/21018 | 4/1999 |
| WO | WO 2006/078204 | 7/2006 |

OTHER PUBLICATIONS

European Search Report dated Jan. 19, 2011 issued in corresponding European Application No. 10180927.5.

* cited by examiner

*Primary Examiner* — Hezron E Williams
*Assistant Examiner* — Hoang Nguyen
(74) *Attorney, Agent, or Firm* — Harness, Dickey & Pierce, P.L.C.

(57) ABSTRACT

The present invention relates to a device (1) for sensing a fluid, such as in a ventilation duct, comprising a sensing element (6), a first housing portion (27) adapted to be arranged outside said object and accommodating the sensing element (6), a supply opening (13) and an outlet opening (37), which openings provide communication between the said first housing portion (27) and the object containing the fluid that is to be sensed. The device (1) further comprises a second housing portion (28), adapted to be arranged outside said object and accommodating electrical connection components, wherein said first and second housing portions (27, 28) are arranged and configured such that they may be connected to each other in geometrically different configurations by use of mechanical fastening means (22) and electrical interconnection means (19, 26).

20 Claims, 4 Drawing Sheets

FLUID DETECTOR

FIELD OF THE INVENTION

The present invention relates to a device for sensing a fluid, such as in a ventilation duct, comprising a sensing element, a first housing portion accommodating the sensing element, and a supply duct and a discharge duct, which ducts at one end communicate with the first housing portion and which ducts at the other end communicate with said object containing the fluid that is to be sensed.

BACKGROUND OF THE INVENTION

Devices for sensing a fluid, for instance in a ventilation duct, do often have to be mounted in places where the available space is limited. Thus, lack of space is a great problem for mounting such devices.

In WO2006/078204 a device for sensing a fluid, such as in a ventilation duct, is disclosed. Even though the device in WO2006/078204 is relatively compact, there is still a need for improved sensing devices that may be mounted in limited spaces.

SUMMARY OF INVENTION

An object of the present invention is to provide a device for sensing a fluid that may be mounted in limited spaces.

The above and other objects that will be evident from the following description are achieved by a device for sensing a fluid according to the appended claims.

According to one aspect of the invention, a device is provided for sensing a fluid in an object, such as a ventilation duct, comprising a sensing element, a first housing portion adapted to be arranged outside said object and accommodating the sensing element, a supply opening and an outlet opening, which openings provide communication between said first housing portion and the object containing the fluid that is to be sensed. The device further comprises a second housing portion, adapted to be arranged outside said object and accommodating electrical connection components, wherein said first and second housing portions are arranged and configured such that they may be connected to each other in geometrically different configurations by use of mechanical fastening means and electrical interconnection means.

The two housing portions may be mounted to each other such that their undersides, that is, the sides facing the object containing fluid that is to be sensed, are substantially in the same geometrical plane. Alternatively, to get an even more flexible device the two housing portions may be mounted such that their undersides are in two different geometrical planes, for instance such that an arbitrary angle, as a right angle, is formed between the undersides or in a curved formation. Alternatively, the undersides may be transversally displaced in relation to each other, or the relation between the undersides may be any combination of a transversal and angular displacement.

A device that comprises two housing portions, which may be mounted to each other in different geometrical configurations is advantageous, since it provides flexibility for the user mounting it. Such a flexible device enables mounting of the device in spaces where a device with a fixed form may not be mounted due to lack of space. The mounting conditions may vary a lot between different mounting places. That is, at one place the space may be limited in one horizontal direction, but at another place the limitation may be at some other horizontal direction. Alternatively, the limitation may be such that in a horizontal direction there is room only for the first housing portion and the second housing portion may have to be mounted transversally displaced in relation to the first housing portion, or on the side of the first housing portion that is facing away from the object containing fluid. At still an additional place, the only possibility to mount the device may be curved around the object containing fluid that is to be sensed. A device according to a design described above may be mounted independently of mounting conditions described above.

Also, in all geometrical configurations described above, the second housing portion may be substantially shielded from the first housing portion. Thus, the second housing portion is separated from the passing fluid, which simplifies access for a user for installation and maintenance. It is also avoided that the connection components are subjected to any substantial influence from the fluid and any potential harmful substances in the same.

According to at least one exemplary embodiment, the mechanical fastening means for connecting the first and second housing portions may be screws, threads, clips, snap fits, or other suitable fastening means. The sets of electrical interconnection means of the first and second housing portions may be electrical contact pads, flexible cables, or the like, as far as the sets of electrical interconnection means of the first housing portion and the corresponding set of electrical interconnection means on the second housing portion are matching each other.

According to at least one exemplary embodiment, said first housing portion comprises at least a first and second set of electrical interconnection means, and said second housing portion comprises a corresponding set of electrical interconnection means, adapted to be connected to either one of said at least a first and second sets of electrical interconnection means of said first housing portion.

Such a first housing portion with at least two sets of electrical interconnection means results in at least two possible configurations, which increases the probability of being able to mount the device in a desired place with limited available space. Since the first housing portion may have to be at a certain position in relation to the object containing the fluid that is to be sensed, it is beneficial for the first housing portion to have at least two sets of electrical interconnection means, while the second housing portion may have only one set of electrical interconnection means, for enabling that the second housing portion may be moved in relation to the first housing portion. Thus, there are at least two possible geometrical configurations.

According to at least one exemplary embodiment, said first and second sets of electrical interconnection means are arranged around a circumference of the first housing portion wherein the shortest arc between the centres of the sets measures 45 to 180 degrees.

That is, in case of two sets of electrical interconnection means on the first housing portion, the distance around the circumference between the centres of two sets may be equivalent or different. Such a distance between the electrical interconnection means provides a device having two possible remarkably different configurations, which further increases the probability of being able to mount the device in a desired place with limited available space, since there may be sufficiently space on one side of e.g. the ventilation duct, but not on the other side. In this context the word arc is to be considered as, in case of a non-circular first housing portion, an arc on an imaginary circle that encircles the first housing portion.

That is, if the first housing portion is quadrangular the arc consequently refers to an arc on a circle that encircles the quadrangle.

In case of three sets of electrical interconnection means, the arcs between the centres of each set may, but need not, be equal, that is measure 120 degrees each. In case of different distances between the sets, the length of each of the two shortest arcs between the centres of the sets may measure 45 to 180 degrees, provided that the sum of the arcs does not exceed the total circumference. In different applications different distances between the sets may be preferable due to the geometrical configuration of the available space at desired mounting places. Also, certain distances may be advantageous, if certain space configurations are more frequent than others.

According to at least one exemplary embodiment, said first housing portion comprises four sets of electrical interconnection means, which are arranged equidistant from each other around a circumference of said first housing portion.

That is, in case of four or more sets, the arcs between the centres of each set may be equal, that is 360 degrees divided with the number of sets. Alternatively the distance between the centres of each set may be different, analogously to the arcs in case of three sets of electrical interconnection means. Several sets of electrical interconnection means increase the number of possible geometrical configurations of the device. In other words, every additional set of electrical interconnection means results in an additional possible geometrical configuration for the assembled device.

According to at least one exemplary embodiment, said first housing portion comprises a first set of electrical interconnection means, which is movably arranged, and said second housing portion comprises a second set of electrical interconnection means, wherein said first and second sets of electrical interconnection means may be connected to each other at different locations around the circumference of the first housing portion.

A device comprising such a movable set of electrical interconnection means has an enormous number of possible configurations, since the second housing portion may, depending on the configuration of the mechanical fastening means, be connected to the first housing portion at a plurality of different positions along the circumference of the first housing portion. Such a set of electrical interconnection means, which may be movably arranged, is for instance a flexible cable, having such a length that the second housing portion and the first housing portion may be connected to each other having a distance between them, provided it is allowed by the mechanical fastening means. Other movable sets of electrical interconnection means is a sliding coupling, which may be moved along at least a part of the circumference of the first housing portion. Alternatively, the first housing portion may be provided with closable openings on a surface which is angled in relation to the object containing the fluid that is to be sensed, through which openings it is possible to insert the set of electrical interconnection means or a flexible cable. The openings that are not used may be closed with suitable closing means. Still alternatively, the first and second housing portions may comprise surfaces which are angled in relation to the object containing the fluid that is to be sensed, which surfaces match each other. That is, said first and second housing portions may be connected to each other such that said surfaces abut against each other. Further, the surface of the first housing portion may comprise at least two openings, each provided with one set of electrical interconnection means, which are aligned with the surface of the first housing portion. The second housing portion may comprise an opening and one corresponding set of electrical interconnection means, which set is also arranged aligned with the surface of the second housing portion. Thus, electrical interconnection is enabled by connecting the first and second housing portions together, using suitable mechanical fastening means, such that the electrical interconnection means of the second housing portion get in contact with one of the sets of electrical interconnection means of the first housing portion. The openings that are not used may be closed with suitable closing means.

According to at least one exemplary embodiment, the first housing portion further comprises a first passage portion for the fluid that is to be sensed, wherein the sensing element is positioned in the first passage portion, the supply opening opens into said first passage portion and a discharge opening is formed in the first passage portion, a second passage portion is by means of a substantially horizontal element substantially shielded from the first passage portion and extends between said discharge opening in the first passage portion and the outlet opening.

With such a design, the fluid can preferably be returned towards the object, for instance a ventilation duct, through the second passage portion after having passed the sensing element. Such a shield allows for arranging the outlet opening almost anywhere on the side of the first housing portion that is facing the object. Especially, the outlet opening may be arranged in the vicinity of the supply opening, which allows to use a two-duct pipe both as a supply and as a discharge duct. Such a design comprising a two-duct pipe simplifies mounting of the device to the object containing the fluid that is to be sensed, since the user does not have to drill separate holes for each pipe using a drilling template. It will also be appreciated that a device for sensing a fluid may be reversible, that is, the flow direction through the device can be reversed with the function maintained.

According to at least one exemplary embodiment, the substantially horizontal element is a printed circuit board. A printed circuit board may be needed in many potential applications, since the sensing element may have to be able to communicate with for example an associated alarm system. An above described design makes it possible to make use of the printed circuit board as a shield between the first and second passage portion as well, which means that a separate shield is not necessary. Hence, fewer components are needed, which results in a more cost-efficient device. In addition, since a device comprising fewer components may be more compact than a device comprising more components, the space needed for mounting the device may be smaller. Thus, the number of possible mounting places is increased at the same time as the device is easier to mount in limited spaces.

According to at least one exemplary embodiment, the flow path of the fluid that is to be sensed changes direction substantially perpendicularly towards a throughput portion of the sensing element, after passing the supply opening into said first housing portion.

Such a change of the direction of the flow path enables the device to be sufficiently flat in a vertical direction, which is advantageous if the space at the place where the device is supposed to be mounted is limited in that direction as well.

According to at least one exemplary embodiment, the device further comprises a removable and re-applicable cover element, which is connected to the second housing portion and is adapted to cover said first housing portion. A removable cover element simplifies physical access for the user, thus, it is possible to perform service and maintenance with small efforts, for instance when exchanging the sensing element.

According to at least one exemplary embodiment, said second housing portion is visually and physically accessible through an at least partially transparent cover.

The cover of the second housing portion may also be completely transparent. By providing the device with a visually accessible portion, it simplifies for a user to inspect and check that the device is in good condition. Easy physical accessibility makes it possible to perform service and maintenance with small efforts, for instance when exchanging the sensing element.

According to at least one exemplary embodiment, the first housing portion has an essentially circular circumference in a substantially horizontal plane, the supply and outlet openings are connected to a supply duct and a discharge duct, respectively, wherein the supply duct and the discharge duct are arranged as a two-duct pipe, in which the ducts are separated by a wall arranged in the pipe, the two-duct pipe is arranged in the vicinity of the perimeter of, and perpendicularly in relation to, the first housing portion, so that the mouth of the supply duct in the first passage portion is arranged in the vicinity of the throughput portion of the sensing element, and a mouth of the discharge duct is positioned in the vicinity of the mouth of said supply duct, and said second housing portion is substantially shielded from the fluid which is intended to flow through the first housing portion.

With the above design of the supply duct and the discharge duct, only one pipe may have to be installed between the device and the object containing the fluid that is to be sensed. Further, by arranging the supply duct in the vicinity of the throughput portion of the sensing element results in essentially direct supply of fluid to the sensing element. The path of the fluid through the housing from the mouth of the supply duct up to the sensing element will thus be substantially straight without interruptions. Also, by arranging the second housing portion separated from the passing fluid, simplified access for a user for installation and maintenance is ensured. It is also avoided that the connection components are subjected to any substantial influence from the fluid and any potential harmful substances in the same. In an exemplary embodiment, the first housing portion has a circular cylindrical shape, but within the scope of the invention, the first housing portion may alternatively have any other arbitrary shape, such that elliptical or polygonal cylindrical.

According to at least one exemplary embodiment, the first housing portion is formed such that the mechanical fastening means and electrical interconnection means are symmetrically arranged around the circumference of the first housing portion. Symmetrically arranged mechanical fastening means and electrical interconnection means are advantageous also since it allows for using the same mechanical fastening means and electrical interconnection means independently of which geometrical configuration of the device is chosen.

According to at least one exemplary embodiment, the sensing element and its throughput portion are slightly asymmetrically arranged in relation to the centre of the first housing portion. Thus, the area disposable for the supply and discharge duct increases without increasing the diameter of the first housing portion. Hence, such an asymmetric arrangement results in a more compact device.

Generally, all terms used in the claims are to be interpreted according to their ordinary meaning in the technical field, unless explicitly defined otherwise herein. All references to "a/an/the element, device, component, means, step, etc" are to be interpreted openly as referring to at least one instance of said element, device, component, means, step, etc., unless explicitly stated otherwise.

Other objectives, features and advantages of the present invention will appear from the following detailed disclosure, from the attached dependent claims as well as from the drawings.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, where the same reference numerals will be used for similar elements, wherein.

All the figures are highly schematic, not necessarily to scale, and they show only parts which are necessary in order to elucidate the invention, other parts being omitted or merely suggested.

DETAILED DESCRIPTION OF EXEMPLARY EMBODIMENTS

The invention will now by way of example be described in more detail by means of embodiments and with reference to the accompanying drawings.

Figure 1:
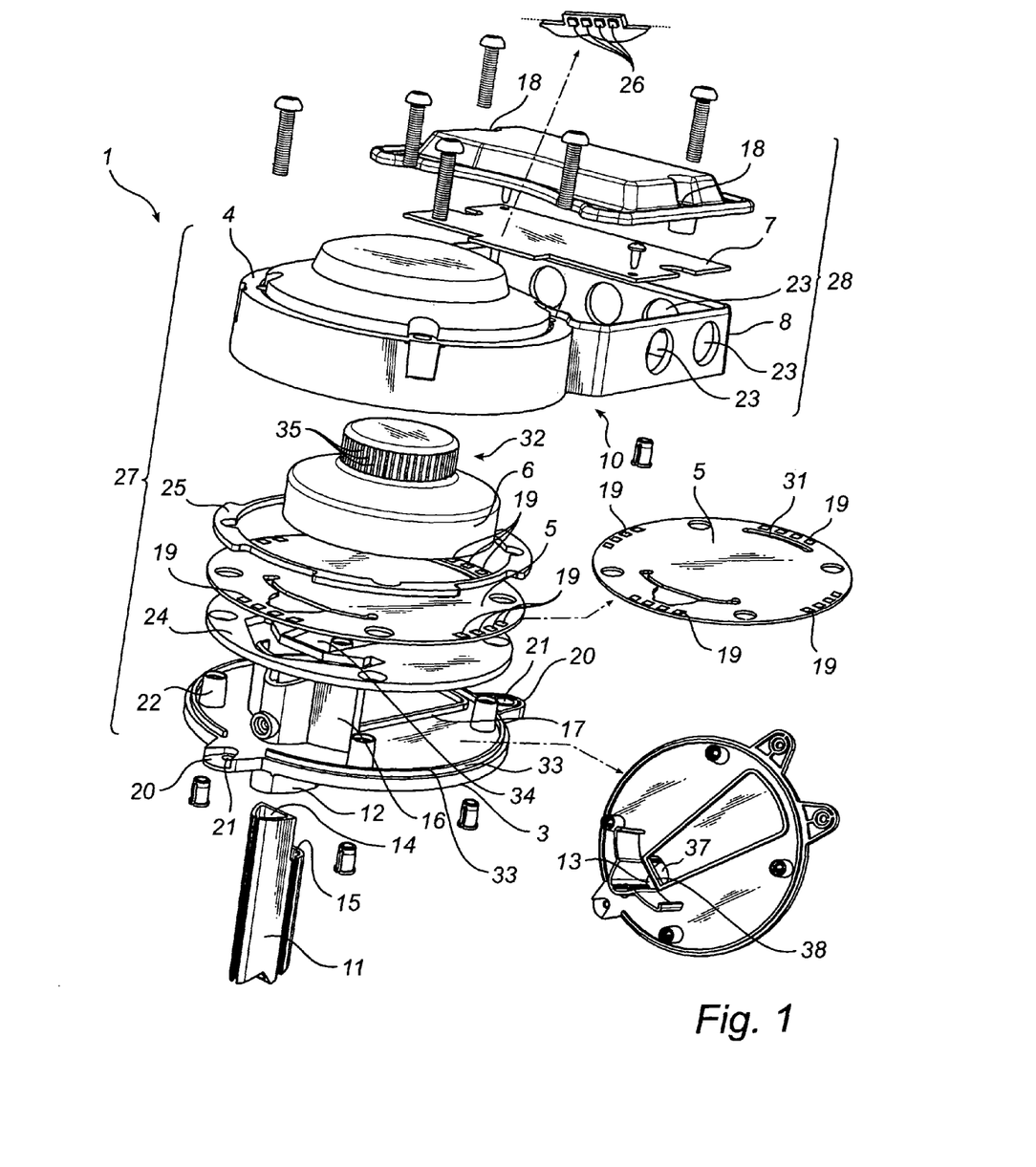
FIG. 1 is an exploded view in perspective of an exemplary embodiment of a device for sensing a fluid according to the invention.
Figure 2:
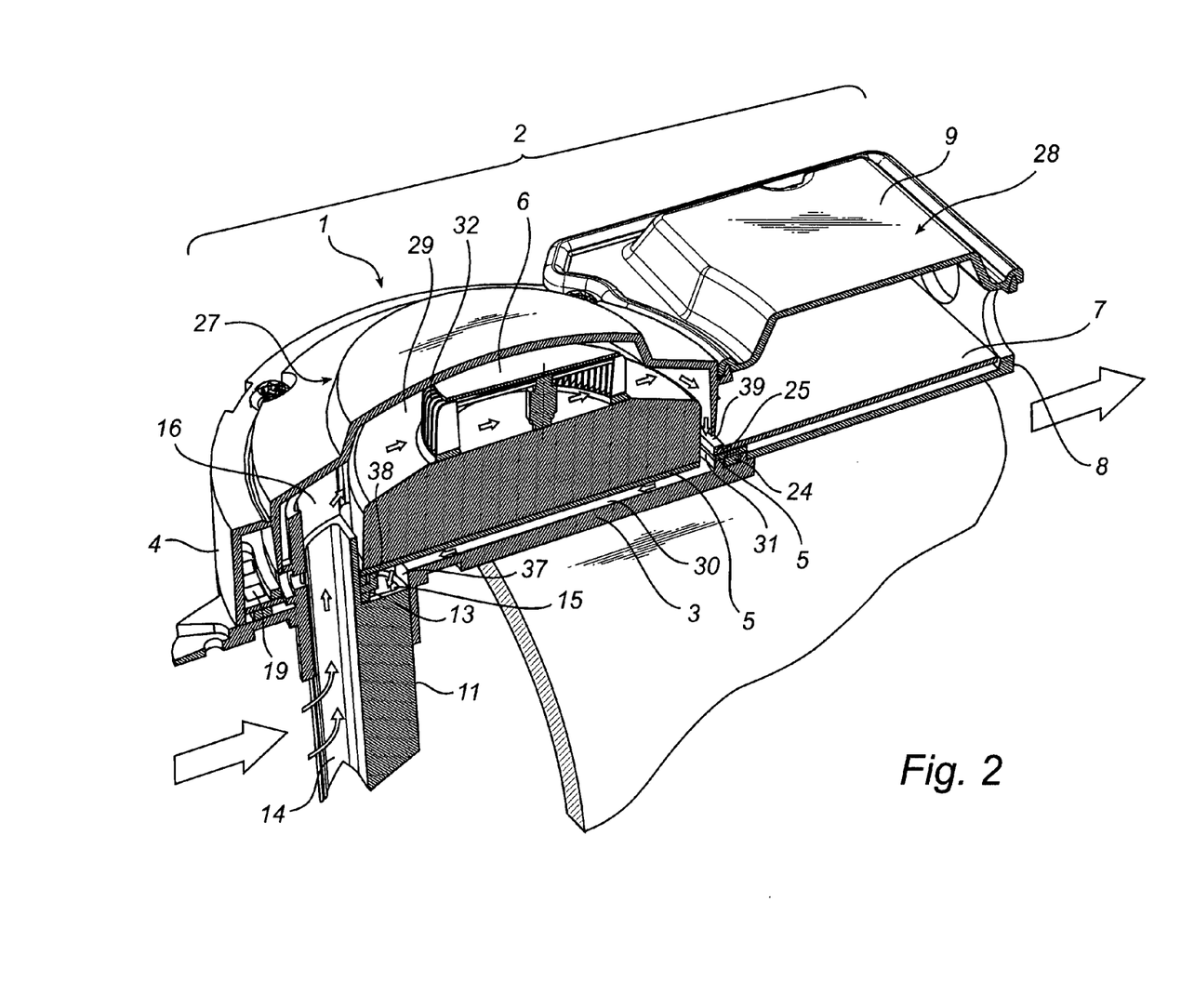
FIG. 2 is a cross-sectional view in perspective of the device according to FIG. 1, for illustrating the path of the fluid through the device.

FIG. 1 is an exploded view in perspective of an embodiment of the invention. It illustrates a device 1 for sensing a fluid in an object, for instance in a ventilation duct. FIG. 2 is a cross-sectional view in perspective of the device according to FIG. 1. The embodiment in FIGS. 1 and 2 has a housing 2, comprising a first housing portion 27 and a second housing portion 28, which first and second housing portions 27, 28 are substantially shielded from each other. A sensing element 6, which consists of a sensing part and a connecting part, is arranged inside the first housing portion 27. The second housing portion 28 accommodates electrical connection components.

The first housing portion 27 is circular cylindrical and the underside of the first housing portion 27 comprises a circular base plate 3, which is formed to be joined to a circular cover element 4. Thus, the circular cover element 4 has substantially the same diameter as the circular base plate 3. The circular cover element 4 is joined together with a housing element 8 for forming a joint cover element 10. In the exemplary embodiment the cover element 10 is formed in one piece. The housing element 8 is described later in connection to the description of the second housing portion 28.

In the assembled position of the device 1, see FIG. 2, the circular base plate 3, a circular printed circuit board 5 and the circular cover element 4 are joined to each other so as to form a first passage portion 29 and a second passage portion 30 in the first housing portion 27.

In the vicinity of the perimeter of the circular base plate 3 and on a side of the circular base plate 3 which is facing the ventilation duct, a connection coupling 12 is arranged to receive a two-duct pipe 11, which extends between the device 1 and the object containing the fluid that is to be sensed. The connection coupling 12 is provided with internal grooves for attachment of the two-duct pipe 11 and the length of the connection coupling 12 is such that the two-duct pipe 11 may be inserted into and retained within the connection coupling 12.

The circular base plate 3 is provided with a supply opening 13 which is adapted to communicate with a supply duct 14 in the two-duct pipe 11, which supply duct 14 is inserted through the supply opening 13. Alternatively, the supply duct 14 may abut against the supply opening 13. An outlet opening 37 is also formed in the circular base plate 3 and separated by a wall 38. A discharge duct 15 of the two-duct pipe 11 abuts against the outlet opening 37.

On the side of the circular base plate 3, which is facing away from the ventilation duct, a flow barrier 16 protrudes from the circular base plate 3 and the supply opening 13. The flow barrier 16 encloses partly an end of the supply duct 14 of the two-duct pipe 11 that extends through the supply opening 13 and a through hole on the circular printed circuit board 5, into the first passage portion 29 of the first housing portion 27. The purpose of the flow barrier 16 is to hinder the fluid from flowing in an undesired direction and together with the circular cover element 4 direct the fluid flow towards the throughput portion of the sensing element 6. The two-duct pipe 11 is adapted to be locked to the circular base plate 3 by a fastening screw, which is inserted through a hole in the flow barrier 16 of the circular base plate 3 to be received in a slit of the two-duct pipe 11.

The side of the circular base plate 3 that is facing away from the object containing the fluid that is to be sensed is provided with a protruding strip 17, extending diametrically from the flow barrier 16 to the opposed side of the perimeter of the circular base plate. The circular printed circuit board 5 arranged on the circular base plate forms the second passage portion 30 together with the protruding strip 17. Furthermore, the second passage portion 30 communicates with the discharge duct 15 of the two-duct pipe 11.

The circular base plate 3 comprises a circular strip 33, extending almost the whole circumference of the circular base plate 3, and which protrudes from the side of the circular base plate 3 that is facing away from the object containing the fluid that is to be sensed. The circular strip 33 having approximately the same height as the protruding strip 17, supports and keeps the circular printed circuit board 5 substantially parallel with the circular base plate 3. Also, the circular strip 33 ensures that a first seal 24, which will be described later, is correctly positioned.

In the exemplary embodiment, the circular base plate 3 comprises four tubes 22 protruding from the side of the circular base plate 3 that is facing away from the object containing the fluid that is to be sensed. The four tubes 22 are arranged in 4-fold rotational symmetry, with regard to the plane of the circular base plate 3, in the vicinity of the circumference of the circular base plate 3.

The circular cover element 4 comprises four tubes (not shown), protruding from a side of the circular cover element 4, which is facing the circular base plate 3 as seen in an assembled position of the device 1. The tubes which are located inside the circular cover element 4 are matching the tubes 22 on the circular base plate 3 regarding both dimension and location. The circular cover element 4 is joined to the circular base plate 3 by inserting the tubes of the circular cover element 4 in to the tubes 22. The circular cover element 4 is mechanically fastened to the circular base plate 3 by inserting one screw through each tube and using corresponding fixation means, such as nuts.

On the circumference of the circular printed circuit board 5 of the first housing portion 27 four sets of electrical interconnection means 19 are arranged equidistantly, that is the arcs between the centres of each set 19 measures 90 degrees. Each set of electrical interconnection means 19 comprises four electrically conductive pads. Alternatively, the shortest arcs between the centres of the sets of electrical interconnection means 19 on the circular printed circuit board 5 may measure from 45 to 180 degrees. The circular printed circuit board 5 comprises also matching through holes adapted for receiving the tubes 22 and the flow barrier 16.

The first and second passage portions 29, 30 are substantially shielded from each other by the circular printed circuit board 5, which forms a horizontal shielding wall between the first passage portion 29 and the second passage portion 30. The first and second passage portions 29, 30 are additionally shielded by a first seal 24. The first seal 24 is circular and provided with through holes adapted to receive tubes 22 and the flow barrier 16. The first seal has also a through recess 34, which is adapted for receiving the protruding strip 17. The first seal 24 is arranged against the circular base plate 3, the circular printed circuit board 5 abutting against the first seal 24 by a pressing force to provide a sealing effect between the circular printed circuit board 5 and the circular base plate 3. The circular printed circuit board 5 may also be fastened to the circular base plate 3 by, for instance, adhesive or the like. It is also possible to fasten the circular printed circuit board 5 by, for instance, double-stick tape, in which case the tape can also act as the sealing element. Also, the first seal 24 may have any other form as long as the intended purpose of the first seal 24 is achieved.

The first and second passage portions 29, 30 are shielded from the environment of the device 1 by the circular cover element 4 and a second seal 25, which is also arranged between the circular cover element 4 and the circular printed circuit board 5 to provide tight-fitting engagement between the circular cover element 4 and the circular printed circuit board 5. The second seal 25 is substantially annular having recesses for the sets of electrical interconnection means 19 and tubes 22. However, within the scope of the invention, the second seal 25 may have any other form as long as the intended purpose of the second seal 25 is achieved.

Consequently, two substantially closed spaces are formed, which means that fluid supplied to the device 1 will essentially flow between the supply duct 14 connected to the first passage portion 29 and the discharge duct 15 connected to the second passage portion 30 through said discharge opening 31, which is arranged as a recess in the circular printed circuit board 5.

In the exemplary embodiment, the circular base plate 3 is provided with mounting portions 20 which are intended for mounting of the device 1 adjacent to the object, for instance a ventilation duct, which contains the fluid that is to be sensed. It is possible to arrange a fitting (not shown) on the object containing the fluid that is to be sensed, in which case the device 1 is mounted on this fitting which then becomes positioned between the device 1 and the object. In the embodiment of the device 1 shown in FIG. 1, the mounting portions, which protrude radially from the circular base plate 3, are provided with fastening through holes 21. The fastening through holes 21 are arranged around the circumference of the circular base plate 3 such that two of the fastening through holes 21 are in vicinity of each other, that is, the arc between the fastening through holes 21 measures approximately 30 degrees and the remaining fastening through hole is on a diametrically opposed side. Each fastening through hole is intended for a fastening screw (not shown). However, the invention is not limited to such a placement of the mounting portions 20, instead the mounting portions 20 may be positioned arbitrarily around the circumference as long as the intended purpose of the mounting portions 20 is achieved. In an exemplary embodiment, it is possible to place the device 1 in an optional position along the circumference of the object containing the fluid that is to be sensed, thereby providing great freedom as to the placing of the device 1.

The sensing element 6, which is known per se, is arranged inside the first passage portion 29 and is in the preferred embodiment formed with a sensing part comprising a detector, such as a smoke detector, and a connecting part, which can be released from each other by a turning motion of the sensing part relative to the connecting part. The sensing part is joined to the connecting part by mechanically and electrically operating connecting means on the sensing part being lockingly engaged with corresponding connecting means on the connecting part in a locking rotary motion of the sensing part relative to the connecting part. The connecting part is preferably screwed to the circular printed circuit board 5 of the first housing portion 27. By removing the cover element 10 from the housing 2, the sensing part can be exchanged in one simple operation, after which the cover element 10 is again mounted on the housing 2. As a result, it is easy to maintain and service the device 1 in case of damage or wear.

The sensing element 6 shown in FIG. 1 is substantially circular in shape and is provided with flanges 35 between which openings are formed. The flanges 35 are arranged in a circumferential direction and constitute a throughput portion 32 for the fluid that is to be sensed. This design makes it possible for the sensing element to take in and sense fluid which flows from all directions around its circumference, whereby sensing will be safe and reliable.

The sensing element 6 is arranged such that it is not centred in relation to the circular printed circuit board 5, instead the sensing element 6 is located as near the discharge opening 31 as possible, such that the area disposable for the supply and discharge ducts 14, 15 increases without increasing the diameter of the first housing portion 27. Hence, the asymmetric arrangement results in a more compact device. Within the scope of the invention the sensing element 6 may also be located in different ways, such as centred or only slightly displaced in relation to the centre of the circular printed circuit board 5.

In the following, the second housing portion 28 according to the exemplary embodiment in FIG. 1 is described. The second housing portion 28 comprises the housing element 8 and a removable protective cover 9. The mainly rectangular housing element 8 is connected to the circular cover element 4 for forming the cover element 10. The mainly rectangular part of the housing element 8 comprises a bottom part and three edge sides. The removable protective cover 9 is formed to be able to close the side of the second space which is facing away from the object containing the fluid that is to be sensed, for protecting the electronics enclosed in the connection space. The protective cover 9 has one through hole 18 in each end and is mounted on the housing element 8 by fastening means, such as screws. The protective cover 9 is in this embodiment at least partially transparent.

The second housing portion 28 is intended to constitute a connection space for connection of electronics to the device 1 and comprises a rectangular printed circuit board, which is arranged horizontally on the bottom part of the second housing portion 28. The rectangular printed circuit board 7 is adapted to carry components that are used for the connection of the device 1 to, for instance, power supply. One side of the rectangular printed circuit board 7 is in use facing the object containing the fluid that is to be sensed and the components that are mounted on the other side of the rectangular printed circuit card 7 faces away from the object containing the fluid that is to be sensed.

The rectangular printed circuit board 7 of the second housing portion 28 is provided with a projection comprising one set of electrical interconnection means 26 corresponding to the sets of electrical interconnection means 19 on the circular printed circuit board 5. The set of electrical interconnection means 26 of the rectangular printed circuit board 7 comprises four electrically conductive pads. Thus, the rectangular printed circuit board 7 may be interconnected electrically, using the set of electrical interconnection means 26, to any one of the four sets of interconnection means 19 on the circular printed circuit board 5 of the first housing portion 27.

The edge sides of the housing element 8 are provided with a number of circular grooves. By applying a force on the material within a groove, the material is eliminated and a through hole 23 is formed. For illustrating the possible positions of the through holes 23, all the circles are punched out in FIG. 1. Such a through hole 23 constitute a bushing for a cable, which may be connected to the rectangular electric circuit board 7 for power supply to the device 1. The through hole 23 has a shape which can receive ordinary cable bushings and sealing plugs, such as membrane bushings. Such grooves make it possible for the person mounting the device 1 to insert the cable to the device 1 at the best position. Alternatively, the housing element 8 may be provided with a number of pre-drilled through holes. After mounting the device 1 to the object, the through holes that are not used, that is, through which the cable is not inserted, may be closed by using suitable closing means, such that plugs or caps.

An edge side of the housing element 8 facing the first housing portion 27 comprises an opening 39, adapted to receive the projection of the rectangular printed circuit board 7 comprising the electrical interconnection means 26. Hence, when the rectangular printed circuit board 7 is arranged in the housing element 8, the electrical interconnection means will project into the first housing portion 27.

The parts of the housing 2 are in the embodiment shown in FIG. 1 arranged to be joined to each other, to form in the joined state a housing 2 with a first housing portion 27, and a second housing portion 28, which housing portions are substantially shielded from each other. The device 1 is assembled by stacking the components of the first housing portion 27 on each other as is illustrated in FIG. 1. That is, the assembling may follow the order described here, but other orders are also possible. On the circular base plate 3 the first circular seal is arranged within the circular strip 33, such that the flow barrier 16, the tubes 22 and the strip 17 are inserted in corresponding through holes or recesses. Thereafter, the circular printed circuit board 5, comprising the sensing element 6, is arranged upon the first seal 24. The second seal 25 is arranged on the circular printed circuit board 5 so that the sets of electrical interconnection means 19 are accessible.

The rectangular printed circuit board 7 is arranged on the bottom of the housing element 8 such that the set of electrical interconnection means 26 on the rectangular printed circuit board 7 is accessible through the opening 39 between the housing element 8 and the circular cover element 4. The protruding strip 17, the circular printed circuit board 5, and the second seal 25 are arranged such that their circumferences provides a sealing effect between the first and second housing portions 27, 28. The protective cover 9 is applied to the housing element 8 by suitable mechanical fastening means such as screws.

The cover element 10 is connected in a desired configuration to the circular base plate 3 using the tubes and the sets of electrical interconnection means 19, 26. The relation between the tubes on the circular cover element 4, the tubes on the circular base plate 3, and all sets of electrical interconnection means 19, 26 is such that once the tubes are matching, the electrical interconnection means 19 on the circular printed circuit board 5 matches automatically the corresponding electrical interconnection means 26 on the rectangular printed circuit board 7. Thus, it is easy for the person mounting the system to apply the cover element 10 to the circular base plate 3 in a desired configuration. In an exemplary embodiment, the cover element 10 may be applied in four different ways by to the circular base plate 3. That is, by rotating the cover element 10, and the components connected to it and forming part of the second housing portion, in its plane and around an axis extending through the centre of the circular cover element 4, the second housing portion 28 is able to be positioned in four different positions around the circumference of the first housing portion 27. Thus, there are four different geometrical configurations, which are shown in FIG. 3a-d.

The cover element 10 is removable and re-applicable, which enables the person mounting the system to remove the cover, change the configuration in a desired way by rotating the cover element 10 as described above, and finally re-apply the cover element 10. In addition, such a removable and re-applicable cover element 10 allows access to the first housing portion 27 to allow, when required, for instance replacement of the sensing element 6 or a filter, or for other maintenance.

Supply and discharge between the device 1 and the object containing the fluid that is to be sensed is, according to the preferred embodiment shown in FIG. 1, arranged by means of a two-duct pipe 11, in which the ducts are separated by a wall arranged in the pipe. The two-duct pipe 11, which comprises the supply duct 14 and the discharge duct 15, is preferably formed in one piece as an extruded pipe, preferably of aluminium. The pipe has a section transversely to the longitudinal direction where the peripheral shape of the circumferential surface that is to be oriented towards the flow is arched and the side which is adapted to be oriented along the flow has a substantially flat circumferential surface. Moreover the supply duct 14 and the discharge duct 15 at the end of the two-duct pipe 11 which is directed away from the housing 2 are closed by, for example, a plug-like element.

In a preferred embodiment, the two-duct pipe 11 is provided with an inlet which is in fluid communication with the supply duct 14. In use, the inlet is arranged in the vicinity of the upstream boundary of the two-duct pipe 11, so that the inlet is substantially facing the main flow direction of the fluid flowing in the object. The orientation of the inlet towards the main flow direction of the fluid in the object allows fluid to flow into the supply duct 14 of the two-duct pipe 11 for further transport to the sensing element 6 which is arranged inside the first housing portion 27.

The two-duct pipe 11 is also provided with an outlet which is in fluid communication with the discharge duct 15, which outlet is positioned downstream of said inlet and upstream of the downstream boundary of the two-duct pipe 11. It has surprisingly been found that the placing of the outlet upstream of the downstream boundary of the two-duct pipe 11 results in a favourable throughput of the partial amount of fluid that is diverted from the object to be sensed by the sensing element 6 inside the first housing portion 27.

In an alternative embodiment (not shown) the circumferential surface of the two-duct pipe 11 which is facing the flow direction of the fluid in the object is provided with a plurality of spaced-apart inlet holes which are distributed along the longitudinal direction of the two-duct pipe 11 and communicate with the supply duct 14. Furthermore the circumferential surface oriented along the flow direction is provided with spaced-apart outlet holes which are distributed along the longitudinal direction of the two-duct pipe and communicate with the discharge duct 15.

The end of the two-duct pipe 11 which is adapted to be inserted into the first housing portion 27 is formed so that the mouth of the discharge duct 15 is positioned radially closer to the centre of the first housing portion 27 than the mouth of the supply duct 14.

FIG. 2 shows how the fluid diverted from the object, preferably a ventilation duct, flows through the device 1 according to a preferred embodiment. The two-duct pipe 11 is provided with an inlet in the circumferential surface of the supply duct 14, said inlet being oriented so that its mouth is oriented towards the flow of fluid in the object. The orientation of the inlet relative to the flow of fluid allows fluid to flow into the supply duct 14. The fluid supplied to the supply duct 14 is then passed on to enter the device 1 through the supply opening 13 which is arranged to connect the mouth of the supply duct 14 to the first passage portion 29 in the first housing portion 27. The mouth of the supply duct 14 in the first passage portion 29 is positioned in the vicinity of the throughput portion of the sensing element 6 to allow a substantially directly directed flow of fluid towards the sensing part. The fluid supplied to the first passage portion 29 of the housing 2 is then, by the flow barrier 16 and the cover element 10, forced to change direction substantially perpendicularly towards a throughput portion of the sensing element 6. The fluid enters through the flanges 35 which are arranged around the sensing element 6 to pass a detector, for instance a smoke detector, which is accommodated in the sensing element 6. Further the fluid flows out through the flanges 35 of the sensing element 6, on the substantially opposite side relative to the side where the fluid enters.

When the fluid supplied to the first passage portion 29 has passed the sensing element 6, the fluid flows into the second passage portion 30 through the discharge opening 31 between the first passage portion 29 and the second passage portion 30. By the mouth of the supply duct 14 and the discharge opening 31 being substantially opposed to each other, with the sensing element 6 positioned between them, a large amount of the fluid supplied to the first passage portion 29 will be forced to pass the sensing element 6, thus ensuring reliable sensing.

The fluid that has flown from the first passage portion 29 to the second passage portion 30 is passed on through the passage which is formed by the second passage portion 30 and extends between the discharge opening 31 and outlet opening 37. Thereafter, the fluid flows through the outlet opening 37 out from the second passage portion 30 and into the discharge duct 15 of the two-duct pipe 11. The discharge duct 15 is further provided with the outlet in the circumferential surface. Thus the fluid supplied to the discharge duct 15 flows out in the object through the outlet arranged in the circumferential surface of the discharge duct 15.

By arranging the flow passage according to the above described configuration of the device 1, a compact design which requires a small installation space is obtained. This is provided by the device having a short overall height in the radial direction of the fluid flow inside the object that is to be sensed. This short overall height is ensured by the fluid being arranged to flow through the device with a substantially longitudinal extent relative to the longitudinal direction of the object.

FIG. 3a-d is a series of sketches showing possible geometrical configurations of a preferred embodiment of the device 1. Since the circular cover element 4 and the housing element 8 are joined together to form the cover element 10, it is possible, by rotating the cover element 10, and the components connected to it and forming part of the second housing portion, in its plane and around an axis extending through the centre of the circular cover element 4, to change the radial extension of the housing element 8 in relation to the centre of the circular cover element 4 without changing the positions of the housing element 8 and the circular cover element 4 in relation to each other. Consequently, the second housing portion 28 is moved around the circumference of the first housing portion 27.

Figure 3A:
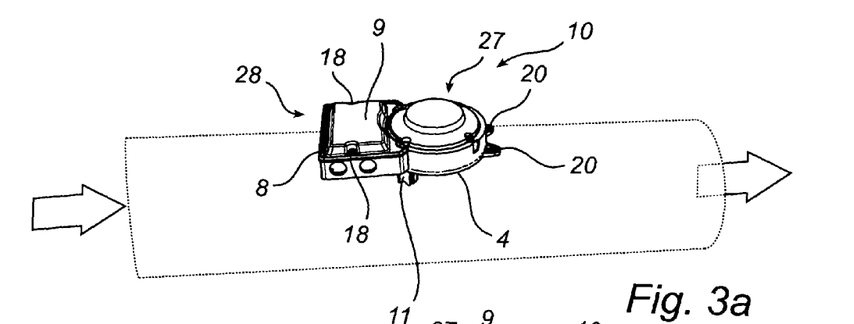
FIG. 3a-d is a sequence of figures illustrating alternative geometrical configurations of a device according to FIGS. 1 and 2.

In FIG. 3a the second housing portion 28 is mounted such that the set of electrical interconnection means 19 of the first housing portion 27 that is used, is located closest to the connection coupling 12 compared to the other sets of electrical interconnection means 19. Hence, the second housing portion 28 is abutting substantially a quarter of the circumference of the first housing portion 27 adjacent to the connection coupling 12 intended for receiving the two-duct pipe 11. Such a configuration is preferable, when the available space extends in the flow direction of the fluid inside the object, but when there is not enough space for the second housing portion 28 downstream of the first housing portion 27, seen in the flow direction of the fluid inside the object.

Figure 3B:
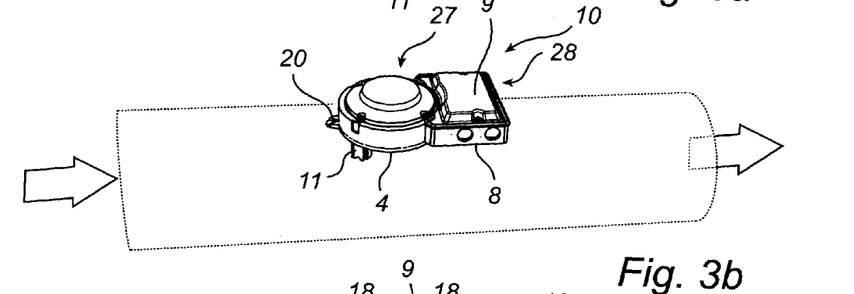

In some cases a configuration shown in FIG. 3b, in which the position of the second housing portion 28 is mirror-inverted along a diameter of the circular base plate 3 in relation to the position of the second housing portion 28 of the configuration in FIG. 3a, is to prefer. It is often necessary to detect the fluid at a certain position in the object containing the fluid that is to be sensed. Depending on surrounding circumstances, it may be impossible to mount the second housing portion 28, due to lack of space, if the device 1 is configured according to FIG. 3a. Such a case may be if there is a wall or some other building construction in the vicinity of the desired position of the two-duct pipe 11. In the configuration in FIG. 3b the second housing portion 28 is mounted such that the set of electrical interconnection means 19 of the first housing portion 27 that is used, is located substantially diametrically opposed in relation to the connection coupling 12. Hence, the second housing portion 28 is abutting substantially a quarter of the circumference of the first housing portion 27, which is opposite to the quarter of the circumference of the first housing portion 27 adjacent to the connection coupling 12 intended for receiving the two-duct pipe 11. Such a configuration may facilitate access to the second housing portion 28 depending on the circumstances at the mounting position.

Figure 3C:
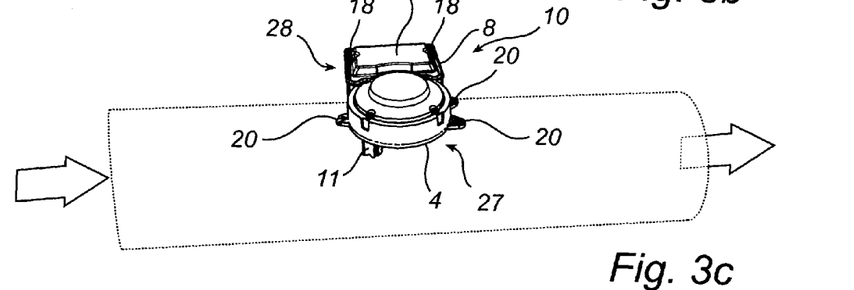
Figure 3D:
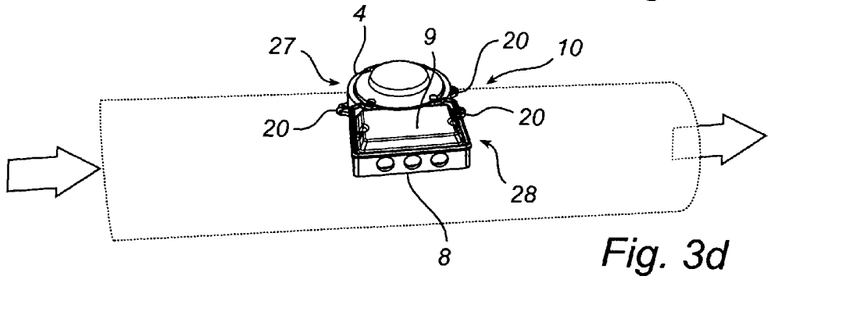

In FIGS. 3c and 3d two additional configurations, which are mirror-inverted in relation to each other, are shown. The second housing portion 28 is mounted such that the set of electrical interconnection means 19 of the first housing portion 27 that is used, is located a quarter of the circumference from the electrical interconnection means 19 located closest to the connection coupling 12. Hence, the cover element 10 is rotated 90 degrees, as is described above, in relation to the configuration in FIG. 3a. The second housing portion 28 is abutting substantially a quarter of the circumference of the first housing portion 27 between the connection coupling 12 and the discharge opening 31. Such configurations may be advantageous if the available space is insufficient in a longitudinal direction of the object containing the fluid that is to be sensed, and sufficient in one of the substantially transverse directions in relation to the longitudinal direction of the object.

Figure 4:
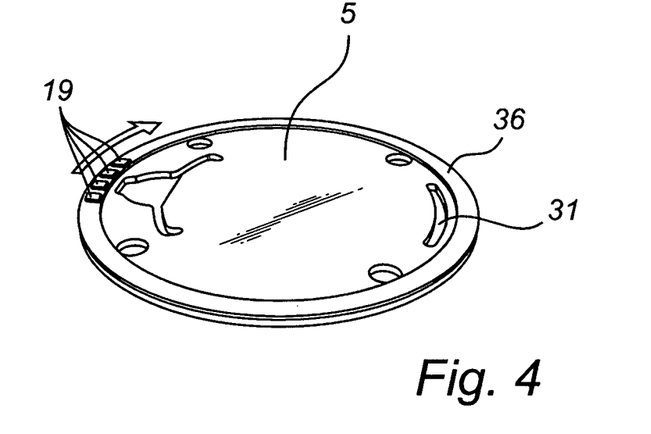
FIG. 4 is perspective view illustrating a movable set of electrical interconnection means according to another exemplary embodiment.

FIG. 4 is a perspective view of a circular printed circuit board 5 according to an exemplary embodiment comprising one set of electrical interconnection means 19, which is movably arranged along the circumference of the circular printed circuit board 5. In the exemplary embodiment the movable set of electrical interconnection means 19 are slidable along the guiding means 36, which extend along the whole circumference of the circular printed circuit board 5.

Although the present invention has been described in connection with particular embodiments thereof, it is to be understood that various modifications, alterations and adaptations may be made by those skilled in the art without departing from the scope of the invention, as defined by the following claims. For instance, the first housing portion 27 may have another shape than circular cylindrical, such as elliptical cylindrical, and the second housing portion 28 may also have another shape than described above, such as mainly quadratic or other polygonal shape.

However, the invention is not limited to four sets of interconnection means 19, there may be fewer or more sets. Regardless of number of sets 19, the arcs between the centres of the sets of electrical interconnection means 19 may measure from 45 to 180 degrees. Alternatively, the whole circumference of the circular printed circuit board 5 of the first housing portion 27 may be provided with electrical interconnection means 19, or the circular printed circuit board 5 may be provided with one set of movable electrical interconnection means. Such movable electrical interconnection means may be moved around whole circumference of the circular printed circuit board 5 of the first housing portion 27. The set of movable electrical interconnection means may be a sliding coupling, which may be moved along at least a part of the circumference of the first housing portion 27. Within the scope of the invention, the circular printed circuit board 5 of the first housing portion 27 may also be provided with flexible cables as electrical interconnection means, which cables enable movement of the second housing portion 28 around the circumference of the first housing portion 27. Alternatively, the first housing portion 27 may be provided with closable openings on the envelope surface of the circular cover element 4, through which openings it is possible to insert the set of electrical interconnection means 26. The openings that are not used may be closed with suitable closing means. Still alternatively, the first and second housing portions 27, 28 may have envelope surfaces, that is surfaces which are angled in relation to the object containing the fluid that is to be sensed, that are matching each other, and the first and second sets of electrical interconnection means 19 of the first housing portion 27 may be arranged in openings as described above, but aligned with respectively envelope surface. The corresponding set of electrical interconnection means 26 of the second housing portion 28 may be arranged aligned with the envelope surface of the second housing portion 28, so that electrical interconnection is enabled by connecting the first and second housing portions 27, 28 together, resulting in that the electrical interconnection means 26 of the second housing portion 28 get in contact with one of the sets of electrical interconnection means 19 of the first housing portion 27. The openings that are not used may be closed with suitable closing means.

Within the scope of the invention, other number or types of electrical interconnection means 19 of the circular printed circuit board 5 are also possible. The number of conductive pads may also be varied, for instance to six. The type of the set of electrical interconnection means 26 of the rectangular printed circuit board 7 may also be varied as far as they match and may be connected to the electrical interconnection means of the circular printed circuit board 5.

The number of tubes 22 on the circular base plate 3 as well as on the circular cover element 4 is not limited to four, but may within the scope of the invention be any arbitrary number as long as the circular cover element 4 is maintained tightly on the circular base plate 3. Alternatively, there may be a larger number of tubes 22 on the circular base plate 3 than on the circular cover element 4, e.g. in case of movable sets of electrical interconnection means 19, for providing more alternative geometrical configurations. Also the tubes 22 may be internally threaded for receiving screws. However, it is possible to arrange the cover element 10 on the housing 2 in other ways, for instance by threads, clips, snap fits etc.

It will be appreciated that the protective cover 9 of the second housing portion 28 can also be formed with locking means which project at each end thereof and is formed with a through hole that is adapted to snap-lockingly engage a projection which is arranged on the housing element 8.

Within the scope of the invention, the cover element 10 may also, in addition to being formed in one piece, be formed of two or more pieces. The pieces may be attached to each other for instance by welding, or by using suitable fastening means, such as a groove and a matching rail. The circular cover element 4 may also comprise a separate removable and re-applicable cover for facilitating access to the first housing portion 27 for instance for allowing replacement of the sensing element 6. The cover element 10, the circular base plate 3, and the protective cover 9 are suitably made of a polymer material, such as polycarbonate (PC) by injection moulding. The cover element 10 and the protective cover 9 may also be at least partly transparent. However, a person skilled in the art realises that these parts can be made of alternative materials without affecting the function of the device 1.

In an exemplary embodiment a fan (not shown) is arranged between the inlet and the outlet to the object containing the fluid that is to be sensed. The fan may enhance or produce a throughput of the fluid that is to be sensed.

In an embodiment, a replaceable filter (not shown) is preferably connected to the supply opening 13 in the first passage portion 29 of the circular base plate 3. The filter is adapted to prevent potential dirt particles in the air flowing into the device from entering the sensing element 6. It will be appreciated that the filter can be arranged anywhere between the supply duct mouth in the object containing the fluid that is to be sensed and the sensing element 6.

In an embodiment, the circular cover element 4 may also be provided with a closable measuring hole (not shown), which allows access for testing the function of the device 1 after installation. The measuring hole may be closable by a closing means which preferably is designed so that, at the end opposite the part closing the measuring hole, it is connected to the circular cover element 4, in which case the closing means does not come loose from the circular cover element 4 when opening the measuring hole. This reduces the risk of losing the closing means when opening the measuring hole. In addition, the circular cover element 4 may also be provided with projecting portions which are adapted to provide a good grip when removing the cover element 10 from the circular base plate 3 and mounting it on the same.

A flow indicator (not shown) may be arranged to be visually visible in the first passage portion 29 of the first housing portion 27. It will be appreciated, however, that a flow indicator may be arranged anywhere in the flow passage between the inlet and the outlet of the object containing the fluid that is to be sensed. However, the cover element 10 has to be at least partially transparent for enabling the flow indicator to be visible. In one embodiment, the flow indicator is formed as a thin foil-like band. One end of said foil-like band may be attached to the circular cover element 4. When said flow indicator is positioned inside the housing 2 in the flow passage of the fluid, the band is set in motion by the passing fluid. The movement of the band due to the flowing fluid provides a visually readable indication that fluid is flowing through the device 1.

In an alternative embodiment, the flow indicator may be designed as a slightly turned plate which is suspended by two torsion wires (not shown). The fluid flowing in the device 1 makes the plate oscillate, thereby providing a visually readable indication that fluid is flowing through the device 1. It is also possible to provide the device 1 with an electronic flow indicator, which for instance emits a signal indicating that a flow of fluid flows through the device.

The device 1 for sensing a fluid may be used in a variety of fields. For instance, such a device can be used to sense a fluid to identify the possible presence of different kinds of particles and/or gases, such as flue gas, carbon dioxide, oxygen, carbon monoxide, laughing gas, hydrocarbons etc. The device can also be used to register, for example, the amount of moisture in a fluid or to register the temperature of a fluid. It will be appreciated by a person skilled in the art that with a device 1 it is also possible to simultaneously sense a plurality of the parameters stated above by way of example. Consequently what can be sensed by the device 1 is determined by the type of detector which is arranged in the sensing part.

The device 1 for sensing a fluid may be used for sensing a fluid in a variety of ducts in buildings, such as ventilation ducts. The ducts may also be located in attics or outdoors.

The invention claimed is:

1. A device configured to sense a fluid, comprising:
a sensing element,
a first housing portion adapted to accommodate the sensing element,
a supply opening and an outlet opening, in which the supply and the outlet openings provide communication between said first housing portion and the fluid that is to be sensed, and
a second housing portion, adapted to accommodate electrical connection components,
wherein said first housing portion includes at least first and second sets of electrical interconnection devices, and said second housing portion includes corresponding sets of electrical interconnection devices, adapted to be connected to either one of said first or second sets of electrical interconnection devices of said first housing portion, and
wherein said first and second housing portions are arranged and configured to be connected to each other thereof in geometrically different configurations by use of mechanical fastening devices and by connecting said sets of electrical interconnection devices of said second housing portion to either the first or second sets of electrical interconnection devices of said first housing portion.

2. The device according to claim 1, wherein said first and second sets of electrical interconnection devices are arranged around a circumference of the first housing portion, wherein a shortest arc between the centers of the sets of electrical interconnection devices measure 45 to 180 degrees.

3. The device according to claim 1, wherein said first housing portion comprises four sets of electrical interconnection devices, which are arranged substantially equidistant from each other around a circumference of said first housing portion.

4. The device according to claim 1, wherein the first housing portion further comprises a first passage portion, wherein the sensing element is positioned in the first passage portion, the supply opening opens into said first passage portion and a discharge opening is formed in the first passage portion, and a second passage portion is provided via a substantially horizontal element substantially shielded from the first passage portion and extends between said discharge opening in the first passage portion and the outlet opening.

5. The device according to claim 4, wherein the substantially horizontal element is a printed circuit board.

6. The device according to claim 1, wherein a flow path of the fluid that is to be sensed changes direction substantially perpendicularly towards a throughput portion of the sensing element, after passing through the supply opening into said first housing portion.

7. The device according to claim 1, further comprising a removable and re-applicable cover element, which is connected to the second housing portion and is adapted to cover said first housing portion.

8. The device according to claim 1, wherein said second housing portion is visually and physically accessible through an at least partially transparent cover.

9. The device according to claim 1, wherein the first housing portion has an essentially circular circumference in a substantially horizontal plane, the supply and outlet openings are connected to a supply duct and a discharge duct, respectively, wherein the supply duct and the discharge duct are arranged as a two-duct pipe, in which the ducts are separated by a wall arranged in the pipe, the two-duct pipe is arranged in a vicinity of the perimeter of, and perpendicularly in relation to, the first housing portion, so that a mouth of the supply duct in the first passage portion is arranged in a vicinity of a throughput portion of the sensing element, and a mouth of the discharge duct is positioned in a vicinity of the mouth of said supply duct, and said second housing portion is substantially shielded from the fluid which is intended to flow through the first housing portion.

10. A device for sensing a fluid, comprising:
a sensing element;
a first housing portion adapted to accommodate the sensing element;
a supply opening and an outlet opening, in which the supply and outlet openings provide communication between said first housing portion and the fluid that is to be sensed; and
a second housing portion, adapted to accommodating electrical connection components,
wherein said first and second housing portions are arranged and configured such that the first and second housing portions are connected to each other in geometrically different configurations by use of mechanical fastening devices and electrical interconnection devices, and
wherein said first housing portion includes a first set of electrical interconnection devices, which is movably arranged, and said second housing portion includes a corresponding set of electrical interconnection devices, wherein said sets of electrical interconnection devices of the first and second housing portions are connected to each other at different locations around a circumference of the first housing portion.

11. The device according to claim 1, wherein the first housing portion further comprises a circular base plate, which includes the supply opening and the outlet opening.

12. The device according to claim 11, wherein the supply opening is adapted to communicate with a supply duct in a two-duct pipe, in which the supply duct is inserted through the supply opening.

13. The device according to claim 12, further comprising a flow barrier protruding from the circular base plate and the supply opening,
wherein the flow barrier encloses partly an end of the supply duct of the two-duct pipe that extends through the supply opening and a through hole on a printed circuit board, into a first passage portion of the first housing portion.

14. The device according to claim 13, wherein a side of the circular base plate that is facing away from an object containing the fluid that is to be sensed is provided with a protruding strip, extending diametrically from the flow barrier to an opposed side of a perimeter of the circular base plate.

15. The device according to claim 11, wherein the circular base plate includes four tubes protruding from a side thereof that is facing away from an object containing the fluid that is to be sensed.

16. The device according to claim 15, further comprising a circular cover element having four tubes protruding from a side of the circular cover element which is facing the circular base plate,
wherein the four tubes of the circular cover element are joined to the circular base plate by inserting the tubes of the circular cover element into the tubes of the circular base plate.

17. The device according to claim 1, wherein each set of electrical connection devices includes four electrically conductive pads.

18. The device according to claim 1, further comprising first and second passage portions substantially shielded from each other by a printed circuit board, which forms a horizontal shielding wall between the first passage portion and the second passage portion.

19. The device according to claim 18, further comprising a first seal provided between the printed circuit board and a circular base plate, to provide additional shield for the first and second passage portions.

20. The device according to claim 18, further comprising a second seal provided between the printed circuit board and a circular cover element, to provide additional shield for the first and second passage portions.

* * * * *